United States Patent
Anderson et al.

(10) Patent No.: US 8,172,895 B2
(45) Date of Patent: May 8, 2012

(54) DESIGN AND ASSEMBLY OF FENESTRATED STENT GRAFTS

(75) Inventors: John Lennon Anderson, Bellevue Heights (AU); David Ernest Hartley, Subiaco (AU); Michael Lawrence-Brown, City Beach (AU)

(73) Assignees: Cook Medical Technologies LLC, Bloomington, IN (US); William A. Cook Australia Pty. Ltd., Queensland (AU)

( * ) Notice: Subject to any disclaimer, the term of this patent is extended or adjusted under 35 U.S.C. 154(b) by 1238 days.

(21) Appl. No.: 11/507,247

(22) Filed: Aug. 18, 2006

(65) Prior Publication Data
US 2007/0142896 A1    Jun. 21, 2007

Related U.S. Application Data

(60) Provisional application No. 60/709,411, filed on Aug. 18, 2005.

(51) Int. Cl.
*A61F 2/82* (2006.01)
(52) U.S. Cl. ............ 623/1.23; 623/1.35; 623/1.11; 623/1.12; 623/1.13
(58) Field of Classification Search ........ 623/1.11, 623/1.12, 1.13, 1.23, 1.32, 1.33, 1.35
See application file for complete search history.

(56) References Cited

U.S. PATENT DOCUMENTS

| | | | | | |
|---|---|---|---|---|---|
| 5,873,906 | A | * | 2/1999 | Lau et al. | 623/1.12 |
| 5,984,955 | A | * | 11/1999 | Wisselink | 623/1.35 |
| 6,395,018 | B1 | * | 5/2002 | Castaneda | 623/1.35 |
| 6,524,335 | B1 | * | 2/2003 | Hartley et al. | 623/1.13 |
| 2002/0193872 | A1 | * | 12/2002 | Trout et al. | 623/1.35 |
| 2004/0054280 | A1 | | 3/2004 | McMorrow et al. | |
| 2004/0171932 | A1 | | 9/2004 | Raman et al. | |
| 2007/0043425 | A1 | | 2/2007 | Hartley et al. | |

FOREIGN PATENT DOCUMENTS

| | | |
|---|---|---|
| EP | 1405613 A1 | 4/2004 |
| WO | 98/53761 A1 | 12/1998 |
| WO | 99/29262 A1 | 6/1999 |
| WO | 01/01864 A1 | 1/2001 |
| WO | 2004/019823 A1 | 3/2004 |
| WO | 2006/007389 A1 | 1/2006 |
| WO | PCT/US2006/032562 | 1/2007 |

* cited by examiner

*Primary Examiner* — David Isabella
*Assistant Examiner* — Suba Ganesan
(74) *Attorney, Agent, or Firm* — Richard J. Godlewski

(57) ABSTRACT

A method of sizing of a stent graft (20) including placement of fenestrations (30, 32) to ensure access to side branch vessels (13, 15) through the fenestrations when the stent graft is introduced into a body vessel and an assembly method for a stent graft including temporary diameter reduction arrangements to enable partial release of a stent graft to assist with positioning of fenestrations with respect to side branch vessels. The method includes spacing the fenestrations to be the same circumferential distance as the side branch vessels irrespective of the diameter of the stent graft.

12 Claims, 7 Drawing Sheets

DESIGN AND ASSEMBLY OF FENESTRATED STENT GRAFTS

CROSS-REFERENCE TO RELATED APPLICATIONS

This application claims priority of provisional application Ser. No. 60/709,411, filed Aug. 18, 2005.

TECHNICAL FIELD

This invention relates to pre-operative sizing and assembly of a stent graft for deployment and more particularly to a stent graft with fenestrations.

BACKGROUND OF THE INVENTION

This invention will be particularly discussed in relation to stent grafts for placement into the thoracoabdominal aorta for the treatment of aneurysms and more specifically in relation to juxtarenal placement. The invention, however, is not so restricted and may be applied to stent grafts for placement in any lumen of the human or animal body.

The segment of aorta between the celiac and renal arteries is the best endowed with adventitial elastin, the most stable, and the last to dilate. Aneurysms of this area are associated with aneurysms of less stable areas in the descending thoracic aorta, infrarenal aorta, or both. Surgical repair of the thoracoabdominal aorta often involves wide exposure through long, multi-cavity incisions, followed by periods of visceral ischemia. Despite advances in surgical technique and perioperative care, the mortality and morbidity rates remain high, especially in patients who are old, sick, or have already undergone open surgical repair of an adjacent segment of the aorta. In such cases, an endovascular alternative would be welcome, yet endovascular methods of thoracoabdominal and pararenal aortic repair have been slow to develop. The challenge has been to exclude the aortic aneurysm while maintaining flow to its visceral branches.

It is roughly 4 years since two distinctly different approaches to this problem were reported. The two devices were: a bifurcated abdominal aortic stent-graft with fenestrations for the renal and superior mesenteric arteries, and a thoracoabdominal stent-graft with branches for the celiac, superior mesenteric and renal arteries. In recent years, the distinctions between fenestrated and multi-branched stent-grafts have been blurred by the emergence of many hybrid devices with features such as Nitinol ringed fenestrations, externally cuffed fenestrations, internally cuffed fenestrations, external spiral cuffs and axially-oriented cuffs or branches, both external and internal. Each element has advantages and disadvantages, and each combination has a different role.

There now exists a family of devices, which share several key features. In each of them, a barbed uncovered Z-stent anchors the proximal end, and a single proximal orifice attaches to a non-dilated segment of aorta (or previously inserted prosthesis). They all distribute blood through multiple branches, cuffs or holes (fenestrations), and they have series of Z-stents and Nitinol rings, providing support from one end of the stent-graft to the other.

In cases of juxtarenal AAA, the rim of non-dilated infrarenal aorta is too short for secure hemostatic implantation of an unfenestrated stent-graft. There is only enough room in the neck for the proximal end of the proximal stent; the rest of this covered stent expands into the aneurysm, assuming a conical shape. Under these circumstances, there is insufficient apposition between the stent-graft and the aorta to achieve a reliable seal. Properly positioned fenestrations (holes) provide a route for flow through the stent-graft into the renal arteries, thereby allowing the proximal end of the stent-graft to be placed higher in the non-dilated pararenal aorta where it assumes a cylindrical shape. The dual goals of renal perfusion and aneurysm exclusion are achieved only when the fenestration is positioned precisely over the renal orifices, and the outer surface of the stent-graft around the fenestration is brought into close apposition with the inner surface of the aorta around the renal orifice. A typical fenestrated technique uses a bridging catheter, sheath or balloon to guide each fenestration to the corresponding renal orifice, and a bridging stent to hold it there. Stent-graft deployment has five main stages: extrusion of the half-open stent-graft, trans-graft renal artery catheterization, complete stent-graft expansion, renal stenting, and completion of the aortic exclusion with bifurcated extension into the iliac arteries.

The three forms of fenestration in common use are the large fenestration, the scallop and the small fenestration. A large fenestration is used only when the target artery is well away from the aneurysm. No bridging stent is required, or even feasible, since one or more stent struts cross the orifice of a large fenestration. A scallop is essentially a large open-topped fenestration. In many cases, the presence of a scallop for the superior mesenteric artery allows sufficient separation (>15 mm) between proximal margin of the stent-graft and the middle of the renal orifices. Small fenestrations are commonly placed over both renal arteries, and held there by bridging stents. Stent struts cannot cross the orifice of a small fenestration. Small fenestrations are therefore confined to the lower halves of the triangular spaces between adjacent stent-struts.

Localized juxtarenal aneurysms or pseudo-aneurysms require no more than a single cylindrical fenestrated stent-graft, but most cases of infrarenal aneurysm extend to the aortic bifurcation and require bilateral iliac outflow through a bifurcated stent-graft. The combination of a fenestrated proximal component with a bifurcated distal component is called a composite stent graft. Dividing the stent-graft into two components separates the two halves of the procedure. The operator need not be concerned about the position or orientation of the bifurcation while inserting the fenestrated proximal component, or about the position and location of the fenestrations while inserting the bifurcated distal component. The composite arrangement also separates the fenestrated proximal component from the large caudally directed hemodynamic forces that act mainly upon the bifurcation of the distal component. A small amount of slippage between the two is preferable to any proximal component migration, where even a few millimeters of movement would occlude both renal arteries. Indeed, the low rate of renal artery loss is testimony to the accuracy of stent-graft deployment and the stability of stent-graft attachment.

The positioning of the fenestration is therefore very important to avoid renal occlusion.

Positioning is further complicated because the diameter of a stent graft is deliberately made larger than the diameter into which it is to be placed to allow for accurate sealing against the vessel wall, possible errors in sizing and subsequent relaxation of the vessel wall. Hence if fenestrations were placed in the same angular position relative to each other on a larger diameter graft than the vessel into which it is to be placed misalignment of the fenestrations with the branch arteries would occur.

A further problem exists that upon deployment and release of the stent graft it is desirable that the graft open up from its confined delivery state to a released position under the influence of self expanding stents with the fenestrations aligned with the renal arteries, for instance. The present invention is also related, therefore, to the problem of assembly or mounting onto a deployment device to assist with accurate release upon deployment.

It is to the pre-operative sizing and placement of the fenestrations on a stent graft and the assembly of a stent graft onto a deployment device that the present invention is directed or at least to provide a practitioner with a useful alternative.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefor the invention is said to reside in a method of pre-operative sizing of a stent graft with at least two fenestrations for placement into a body vessel having an inner wall with side branch vessels and intended for access to the side branch vessels through the fenestrations, the method comprising the steps of;

a) determining the internal diameter of the body vessel at the level of the side branch vessels, b) assessing the angular position of the of each of the side branches from a selected datum position on the vessel, c) converting the angular position to a circumferential distance along the inner wall of the vessel from the selected vessel datum for each of the branch vessels, d) selecting a diameter of stent graft which is 10% to 20% greater than the determined diameter of the vessel, and e) positioning fenestrations on the stent graft such that each is the converted distance calculated in step c) from a stent datum position on the stent.

Preferably the selected datum position on the vessel is the anterior most point in the vessel.

The internal diameter of the body vessel and the angular position of the of each of the side branches can be determined for instance with the use of narrow slice, contrast enhanced computer tomography.

In one embodiment the step of assessing the angular position of the of each of the side branches from a selected datum position on the vessel, comprises defining the angular position as a clock face with the datum position being 12 o'clock and the position of the of each of the side branches being in terms of hours on the clock face.

Alternatively the step of assessing the angular position of the of each of the side branches from a selected datum position on the vessel, comprises defining the angular position in degrees either side of the datum position.

The invention can further comprise the step of temporarily reducing the diameter of the stent graft at least at the level of the fenestrations. Diameter reduction is preferably done at a position diametrically opposite to the stent datum position. The step of reducing the diameter can comprise applying diameter reducing ties.

The step of applying diameter reducing ties can comprise the steps of;

a) extending a release wire longitudinally along the stent graft;

b) looping a flexible thread around the release wire and extending one end of the flexible thread laterally around the circumference of the stent graft to a position a selected distance from the release wire;

c) engaging the flexible thread into the graft material, and d) drawing the ends of the thread together and tying ends of the thread, whereby the selected distance is reduced thereby reducing the overall diameter of the stent graft.

The step of applying diameter reducing ties can further comprise the steps of;

e) passing a second flexible thread around the release wire or the first flexible thread and extending the second flexible thread laterally around the circumference of the stent graft in the opposite direction to the first flexible thread to a position a selected distance from the release wire;

f) engaging the second flexible thread into the graft material, and g) drawing the ends of the second thread together and tying ends of the thread, whereby the selected distance is reduced thereby reducing the overall diameter of the stent graft.

Preferably the circumferential thread extends circumferentially in each direction from the release wire.

There can be two release wires and a circumferential thread extending circumferentially in each direction from each of the release wires.

The step of applying diameter reducing ties can comprise applying a plurality of diameter reducing ties along the length of the stent graft.

In a further form the invention comprises a stent graft prepared by the method discussed above.

In a further form the invention comprises a stent graft for placement in a body vessel, the body vessel having a measured diameter at the level of side branches of the vessel and the side branches being spaced circumferentially on an inner wall of the vessel by a measured distances from a vessel datum point, the stent graft comprising a tubular body of a biocompatible graft material and at least two fenestrations in the tubular body, the tubular body having a diameter of between 10 to 20% greater than the measured diameter of the branch vessel in the region of the fenestrations, the fenestrations being spaced apart circumferentially around the tubular body from a selected graft datum point by the measured distance, whereby when the stent graft is introduced in to the vessel the fenestration can be aligned with the side branches.

Preferably the vessel datum point is an anterior point on the vessel and the graft datum point is the anterior most point on the stent graft.

The stent graft can further comprise a plurality of diameter reducing ties temporarily reducing the diameter, the diameter reducing ties being substantially diametrically opposed to the graft datum point.

The stent graft can further comprise a temporary diameter reduction constraint arrangement at a position substantially diametrically opposed to the graft datum point, the constraint arrangement comprising at least one release wire extending longitudinally along the tubular body and at least one circumferential thread engaged around the release wire and a portion of the stent graft circumferentially spaced a selected distance away from the release wire and drawn tight and tied to reduce the circumference and hence the overall diameter of the stent graft.

It will be seen that by this invention there is provided a fenestrated stent-graft which is a highly customized device, which has a design based largely upon the findings of narrow slice, contrast-enhanced CT, and the expected orientation of the stent-graft. During preoperative sizing, each arterial orifice is located relative to other landmarks up and down the long axis of the aorta, and oriented relative to other points on the same trans-axial section of the aorta. The orientation is described as an angle or as hours and minutes, as though the aorta were a clock face with anterior being 12:00. However, this does not translate directly into the fenestration's position on the fully opened stent-graft, because the stent-graft is not expected to open evenly. The constraining ties in the back of the stent-graft ensure that only the anterior surface opens completely. The posterior surface accommodates any oversizing. The renal fenestrations are therefore positioned so that the length of the arc between them on the anterior surface of the opened stent-graft matches the length of the arc between the arteries which they will oppose on the anterior surface of the aorta at that level.

BRIEF DESCRIPTION OF THE DRAWING

This then generally describes the invention but to assist with understanding reference will now be made to the accompanying drawings which show preferred embodiments of the invention.

In the drawings.

DETAILED DESCRIPTION

Figure 1:
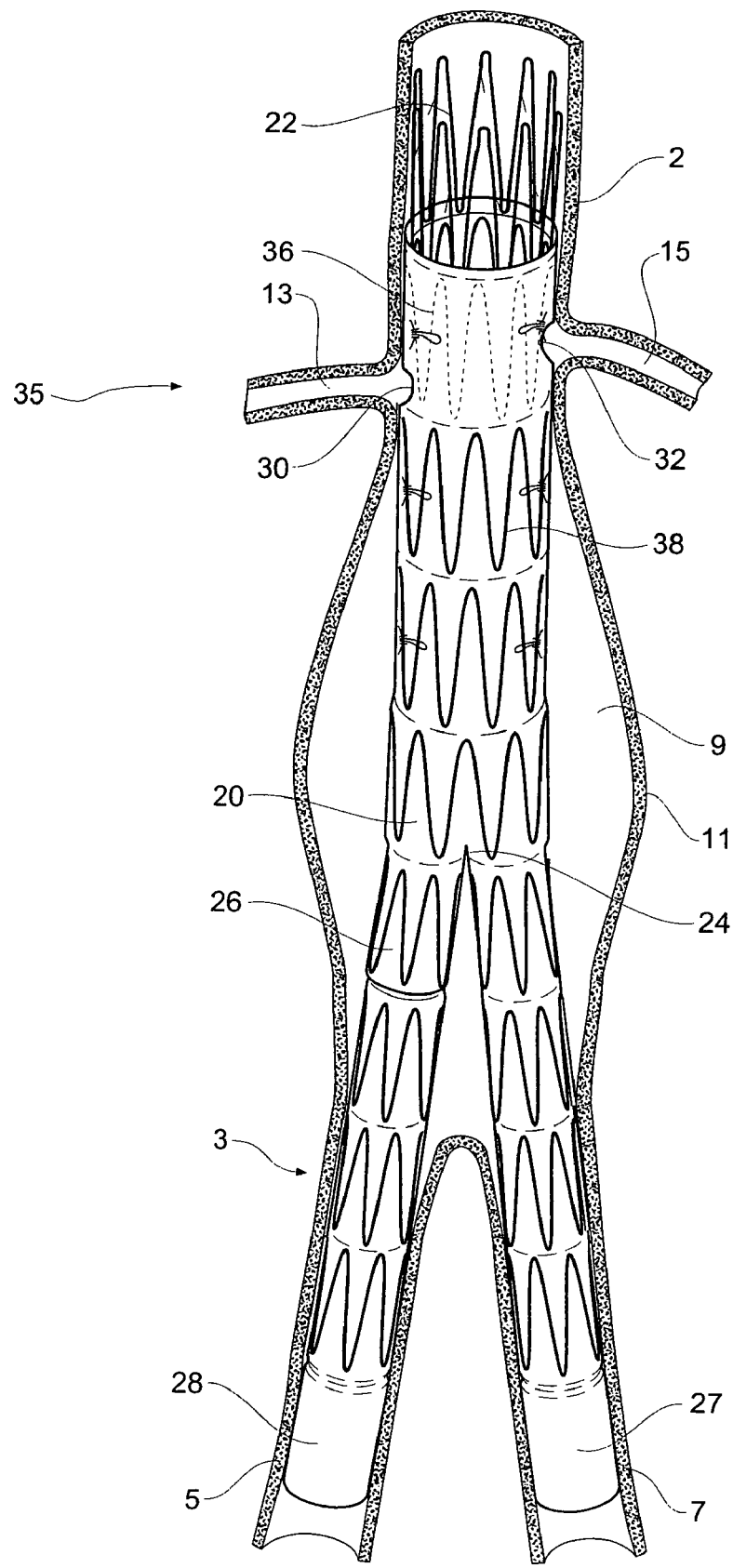
FIG. 1 shows a schematic view of an aneurysed aorta with a bifurcated and fenestrated stent graft deployed into it.

Now looking more closely at the drawings and in particular FIG. 1 it can be seen that there is schematically shown an aorta 2 extending down to an aortic bifurcation at 3 and into two iliac arteries 5 and 7. An aneurysm 9 defined by a bulge in the aorta wall 11 extends from near to the aortic bifurcation 3 nearly to the renal arteries 13 and 15. There is insufficient non-aneurysed length of the aorta distally of the renal arteries and hence to place a stent graft to bypass the aneurysm it is necessary to place some of the stent graft proximally of the renal arteries.

This embodiment of the invention is discussed in relation to a bifurcated stent graft having a longer leg for extending into one iliac artery and a shorter leg into which a leg extension may be deployed for the contralateral iliac artery but the invention is not so limited and may also be used for a composite stent graft in which the fenestrations are in a proximal tubular portion of the composite stent graft and if necessary a further bifurcated portion of stent graft is used to extend down to the iliac arteries.

As shown here a stent graft 20 has a proximally extending exposed stent 22, a proximal internal stent 36 and a plurality of external stents 38 along the length of its tubular body.

The stent graft 20 has a bifurcation 24 and a long leg 27 extending down iliac artery 7 and a short leg 26 directed towards iliac artery 5. A leg extension 28 is connected into the short leg 26 and extends down the iliac artery 5. The stent graft 20 has a proximal internal stent 36 and a plurality of external stents 38 along the length of its tubular body. At the renal arteries 13 and 15 there are fenestrations 30 and 32 respectively for allowing access to the renal arteries and it is to the placement of these renal fenestrations on the stent graft so that they match up with the renal arteries when the stent graft is deployed into the aorta that the present invention is directed.

Methods of mounting a stent graft onto a deployment device and deployment of such a stent graft are described in PCT Patent Publication Number WO98/53761 entitled "A Prosthesis and a Method of Deploying a Prosthesis". These features and other features disclosed in PCT Patent Publication Number No. WO98/53761 could be used with the present invention and the disclosure of PCT Patent Publication Number No. WO98/53761 is herewith incorporated in its entirety into this specification.

Although the renal arteries in FIG. 1 are depicted as extending laterally either side of the aorta, in fact the position of the renal arteries is very variable and they are sometimes closer together towards the anterior surface of the aorta and can be positioned more or less apart longitudinally.

Figure 2:
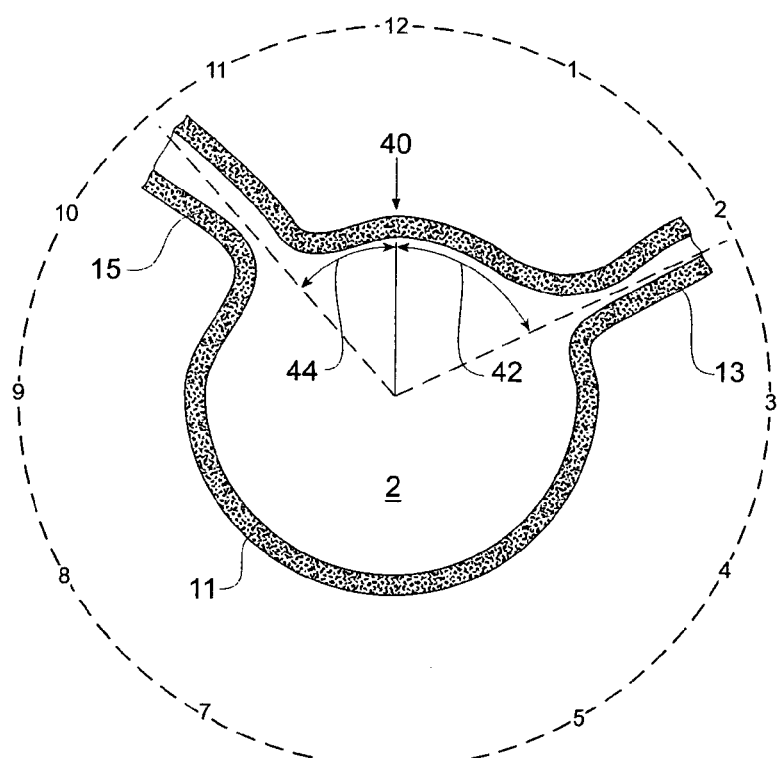
FIG. 2 shows a schematic cross section of the aorta in the renal arteries and shows how the position of the renal arteries with respect to a datum position is determined using a clock face system.
Figure 3:
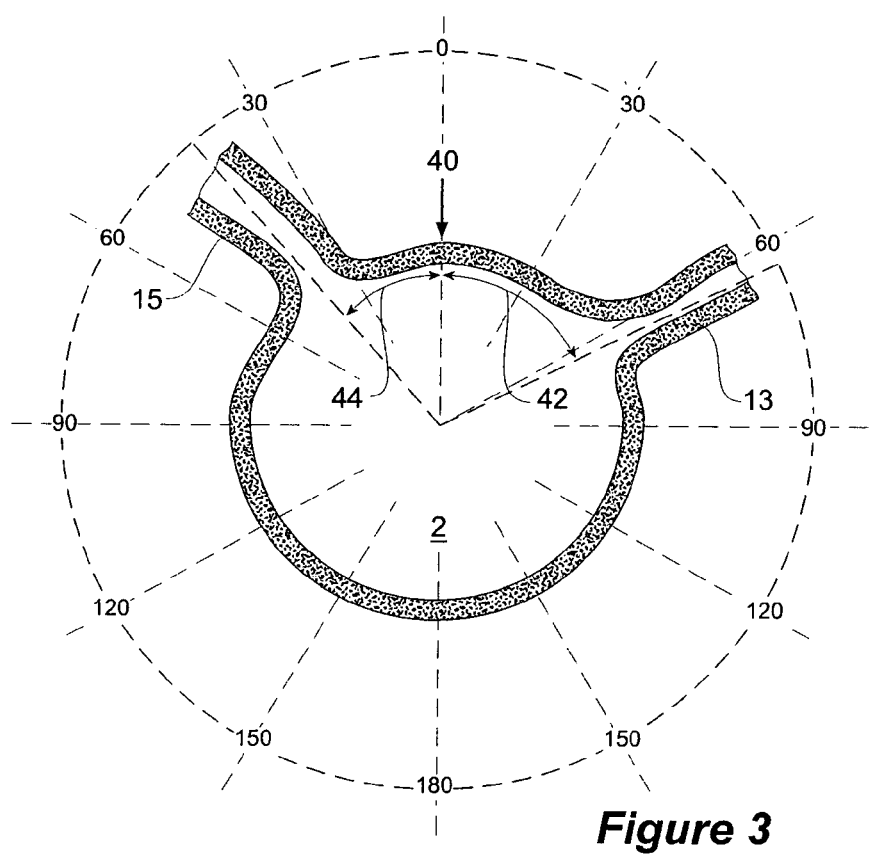
FIG. 3 shows a similar embodiment to that of FIG. 2 except using a method determining the position using angles from a selected datum.

FIGS. 2 and 3 show a schematic cross section of the aorta in the region of the renal arteries indicated by the arrow 35 in FIG. 1.

In FIG. 2 the aorta 2 is defined by an aorta wall 11 and renal arteries 13 and 15 extend from the aorta 2. For the purposes of this invention the renal arteries are depicted as being at the same level in the aorta in FIG. 2 although generally there may be a longitudinal spacing between the left and right renal arteries as is depicted in FIG. 1.

In order to ensure accurate alignment between the fenestrations of a stent graft and the renal arteries it is desirable to place balloon expanded stents or self expanding stent assemblies into the renal arteries from fenestrations in the stent graft being placed into the aorta. Generally a stent graft placed into an aorta has a diameter of perhaps 10 to 20 percent more than the diameter of the aorta and hence if the angular position of the fenestrations, one with respect the to other, were translated from the renal artery to the larger diameter stent graft and the stent graft released into the aorta it is unlikely that it could be possible to easily ensure that the fenestrations open in apposition to the respective renal arteries because it is not possible to guarantee that the stent graft will open evenly within the aorta.

The cross section of the aorta in the region of the renal arteries as shown in FIG. 2 is obtained by radio-graphic techniques such as narrow slice enhanced computer tomography. A datum point 40 on the aorta is selected. This is normally taken as the anterior point on the aorta as this can be most easily ascertained from radiography during deployment. The position of the renal arteries with respect to the datum point 40 is then determined. In FIG. 2 the method used is to assume that the aorta at the level of the renal arteries comprises a clock face with 12 o'clock at the selected datum point 40. This means that the centre of the renal artery 13 is at approximately 2 o'clock and the centre of the renal artery is at approximately 10:30.

In FIG. 3 an alternative arrangement is used in which degrees either side of the datum point 40 are used. In this case the renal artery 13 is at approximately 65 degrees from the datum point 40 to one side and the other renal artery 15 is approximately 40 degrees on the other side of the datum point.

Next, knowing the diameter of the actual aorta 2 the inner circumference of the wall of the aorta is calculated and the circumferential distance 42 from the datum point 40 to the centre of the renal artery 13 and the circumferential distance 44 from the datum point 40 to the centre of the renal artery 15 is calculated.

A stent graft is then selected with a diameter which is 10 to 20 percent greater than the diameter of the aorta 2. For instance if the aorta has a diameter of 30 millimetres at the level of the renal arteries then a stent graft may be selected with a diameter of 36 millimetres at that level. A datum point 41 (see FIG. 4), which corresponds to the position, when the stent graft is deployed, of the selected datum point 40 on the aorta, is then selected on the stent graft and the circumferential distances 42 and 44 are measured on the surface of the stent graft in each direction from the datum point 41 to define centre points for each fenestration and fenestrations are then positioned around those centre points. It will be realised that a certain amount of latitude may be provided to ensure the fenestrations do not interfere with struts of stents on the surface of the stent graft.

Diameter reducing ties are then applied to the stent graft as will be discussed in more detail with respect to FIGS. 7, 8 and 9.

Figure 4:
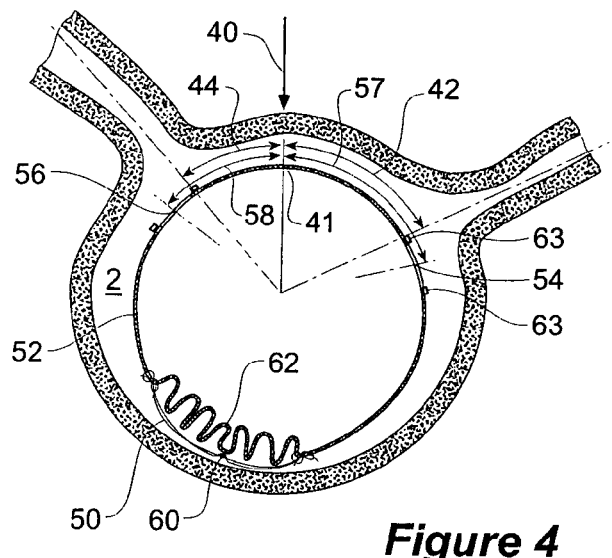
FIG. 4 shows a similar view to that of FIGS. 2 and 3 but with a stent graft in a semi-contracted condition deployed in the aorta but not showing other features of the deployment device upon which the stent graft is deployed.
Figure 5:
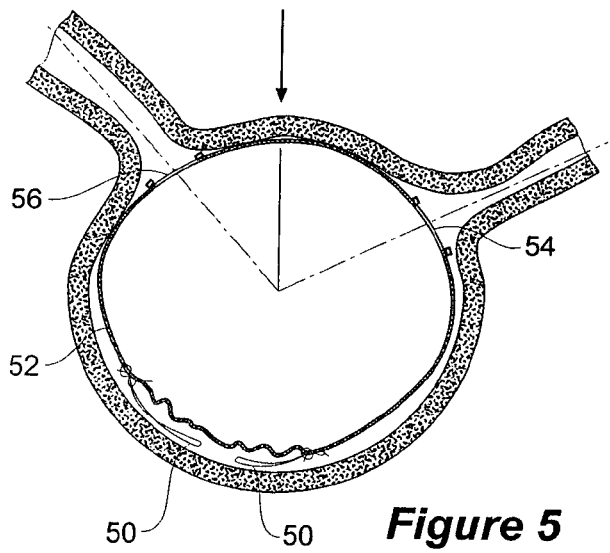
FIG. 5 shows a similar view to that of FIG. 4 except with the diameter reducing ties on the stent graft released.
Figure 6:
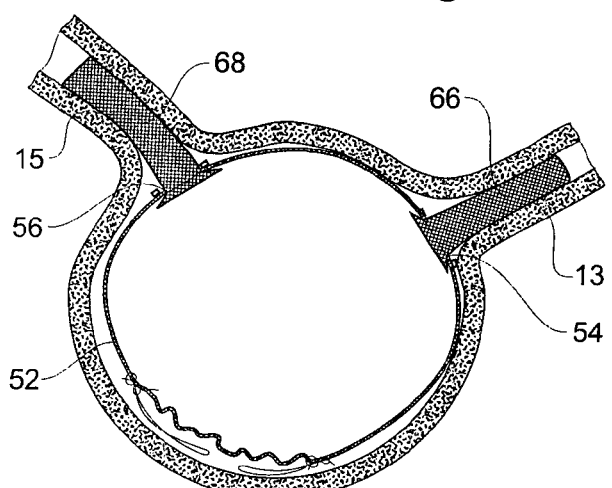
FIG. 6 shows a similar view of FIG. 5 with side graft stents placed in the fenestrations.

For clarity the various components of the deployment device are not depicted in FIGS. 4, 5 and 6.

As depicted in FIG. 4 a stent graft has been partially deployed into the aorta 2 with a sheath (not shown) retracted but the diameter reducing ties generally shown as 50 are still in place so that the overall diameter of the stent graft 52 is somewhat less that the diameter of the aorta 2. At this stage the stent graft can be rotated and moved longitudinally. The stent graft is rotationally positioned so that the datum point 41 on the stent graft is coincident with the selected datum point 40 on the aorta. Observations of the position of the stent graft in the aorta can be made because radiopaque markers on the stent graft can be observed by suitable radiographic techniques. Fenestrations 54 and 56 have been placed so that the distance 57 of the fenestration 54 from the datum point 41 and the distance 58 of the fenestration 56 to the datum point 41 are the same as the distances 42 and 44 respectively as discussed in relation to FIG. 2.

The diameter reducing ties are held in place by a release wire 60. It will be noted that the diameter reducing ties are as far as possible diametrically opposed to the two fenestrations 54 and 56 so that the diameter reduced portion 62 of the stent graft 52 is as far around from the renal arteries as possible.

As shown in FIG. 5 the release wire has been withdrawn so that the diameter reducing ties 50 are released and the stent graft can engage the walls of the aorta.

The actually position of the fenestrations 54 and 56 are defined by radiopaque markers 63 either side of the fenestration 54 for instance and as can be seen in FIG. 5 when the diameter reducing ties are released the stent graft 52 can expand against the walls of the aorta. Generally the corrugated portion of the stent graft which was involved with the temporary diameter reduction does not fully expand so that the circumferential distance between the fenestrations is equivalent to the circumferential distance of the wall of the aorta between the fenestrations and access to the renal arteries through the fenestrations is possible.

FIG. 6 depicts a next stage in the deployment process where balloon expanded stents 66 and 68 have been deployed through the fenestrations 54 and 56 respectively and into the renal arteries 13 and 15 respectively and expanded.

Figure 7A:
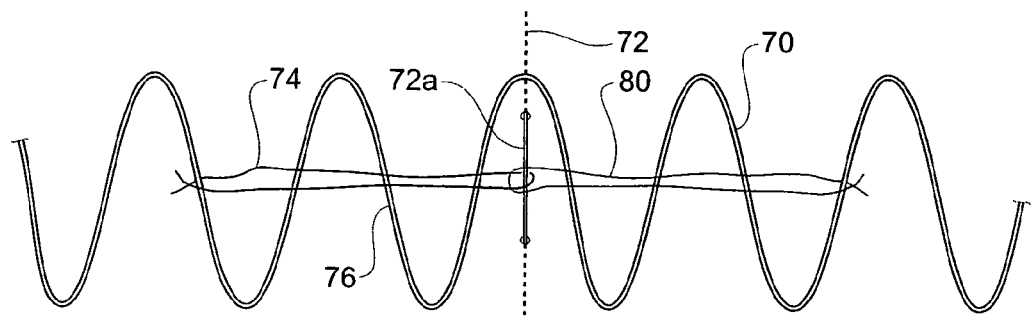
FIGS. 7A and 7B show schematically how one arrangement of a diameter reducing tie is applied to a stent graft.
Figure 7B:
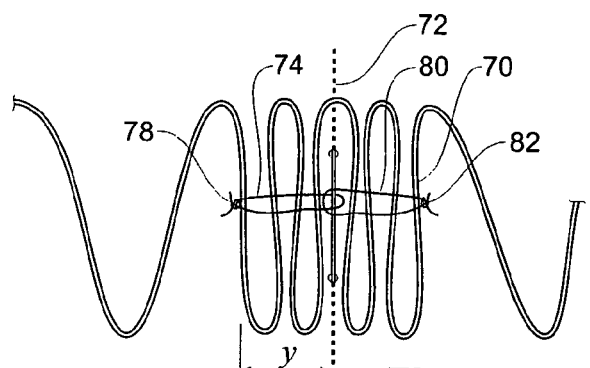

FIGS. 7A and 7B show schematically one embodiment of diameter reducing tie according to the present invention. In this drawing the graft material of a stent graft is not shown and only a portion of a self expanding stent is shown stretched out flat.

As can be seen in FIG. 7A a self expanding stent 70 which would extend around the tubular body of a stent graft and be stitched to the stent graft material is shown. A release wire 72 is stitched longitudinally along the stent graft as can be seen in more detail in FIG. 9A with a stitch 72a being exposed to the outside of the stent graft in the region of the self expanding stent 70.

A first suture thread 74 is passed around the release wire 72 and extended out to one side of the release wire over the struts 76 of the stent graft to pass over three struts and to be looped around a fourth strut and into the graft material. The suture thread 74 is then pulled tight and knotted as shown in FIG. 7B with a knot 78 so that the struts between the release wire 72 and the knot 78 are pulled closer together.

A similar action is carried out to the other side of the release wire with a thread 80. In this case the thread 80 can either pass around the release wire 72 or is passed underneath the two strands of the thread 74 and over the release wire 72, passed over three struts and then it can be passed over three struts and then looped around a fourth strut and into the graft material and pulled tight and knotted at 82.

Figure 8A:
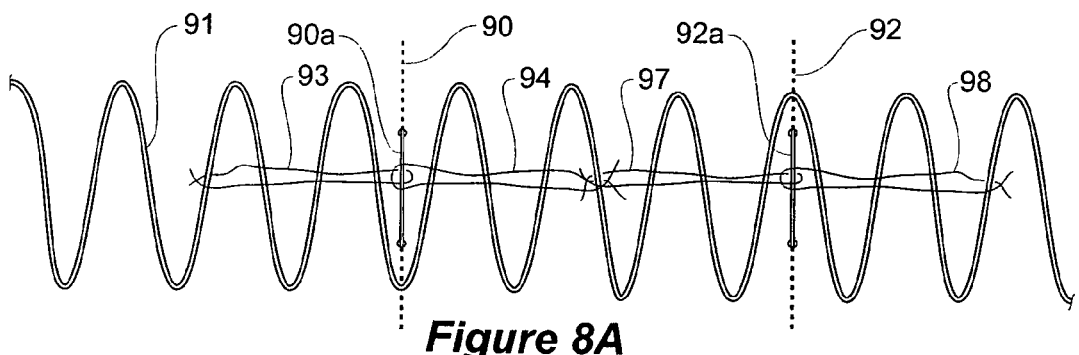
FIGS. 8A and 8B show an alternative embodiment of diameter reducing tie intended for use with a stent graft.
Figure 8B:
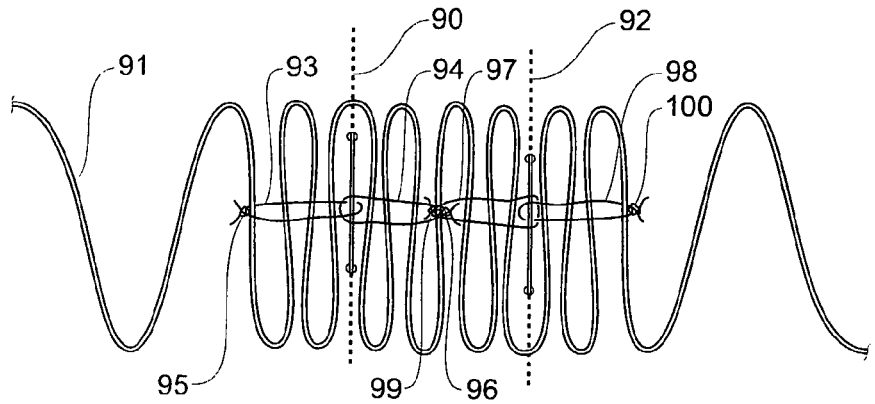

The reduction in distance between the release wire 72 and the knot 78 may be from 50 to 75 percent. For instance if the distance is 15 millimetres round the circumference from the release wire 72 to the strut at which the knot 78 is placed then this can be reduced to 5 millimetres. With two diameter reducing ties one to each side of the release wire 72 therefore a total circumference reduction of 20 millimetres can be achieved which will change the diameter of a 36 millimetre stent graft to approximately 28 millimetres. In the example discussed above this is less than the diameter of the aorta which means that the stent graft will still be manoeuvrable within the aorta while still mounted onto the deployment device but partially freed by the withdrawal of a containing sheath.

Where a greater amount of diameter reduction is desirable double diameter reducing ties may be used as depicted in FIGS. 8A and 8B.

In this embodiment two release wires 90 and 92 are used parallel to each other and spaced apart by 6 or 7 struts of a self expanding stent 91. The two release wires 90 and 92 are stitched longitudinally along the stent graft as can be seen in more detail in FIG. 9A with stitches 90a and 92a being exposed to the outside of the stent graft in the region of the self expanding stent 91. A first suture 93 extends from one side of the release wire 90 and a second suture 94 extends to the other side of the release wire 90 and they are knotted off at 95 and 96. Similarly sutures 97 and 98 are extended either side of the release wire 92 and are knotted off at 99 and 100. Generally the knots 96 and 99 go on either side of the same strut.

By using these double diameter reducing ties for instance a reduction in circumference of up to 40 millimetres may be obtained for a 36 millimetre diameter stent graft which will give a final diameter of approximately 24 millimetres. Once again with this temporary reduction in diameter, movement of the stent graft for final positioning can be easily achieved.

Figure 9A:
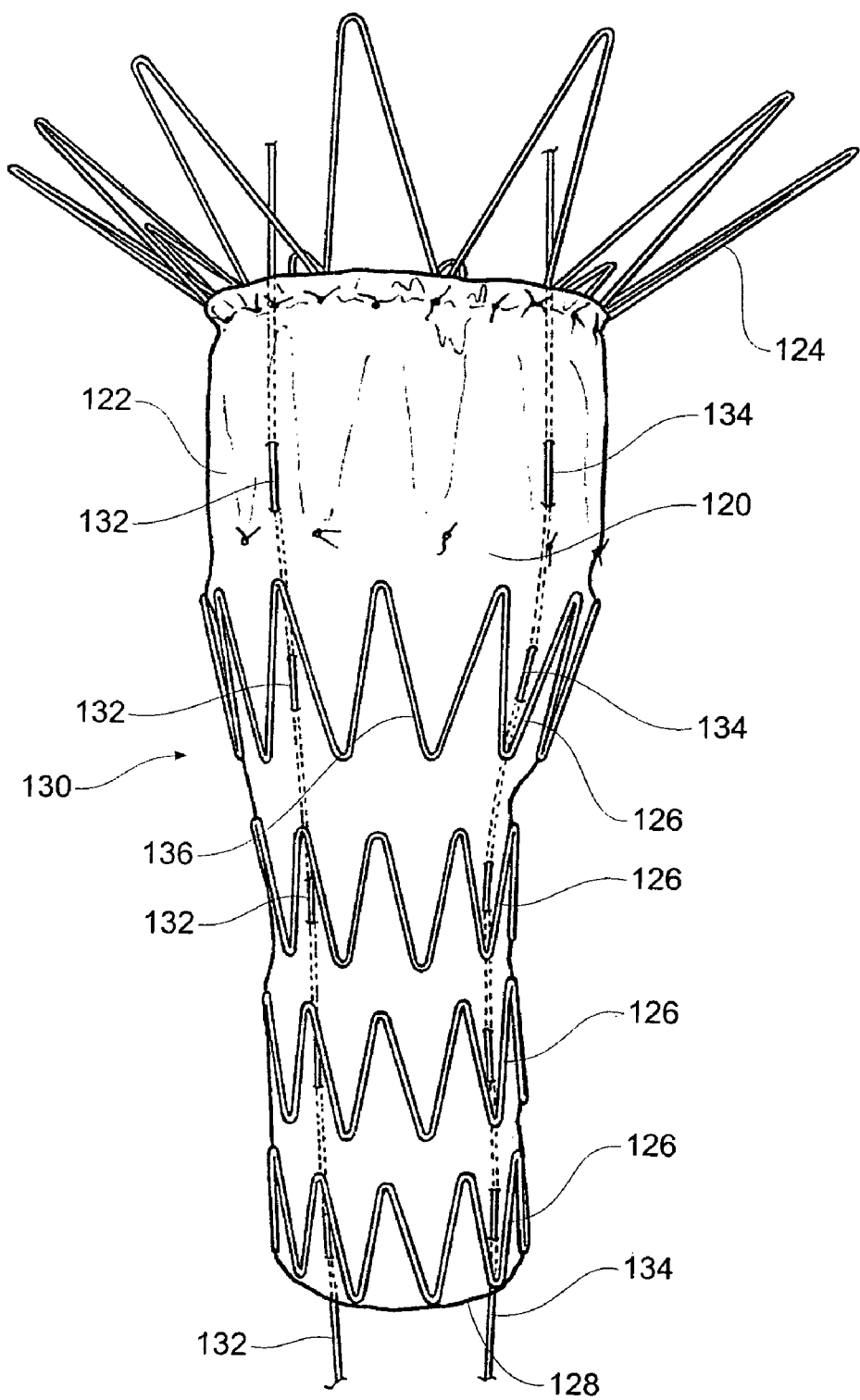
FIGS. 9A, 9B and 9C show a stent graft in various stages of application and release of double diameter reducing ties on a stent graft.
Figure 9B:
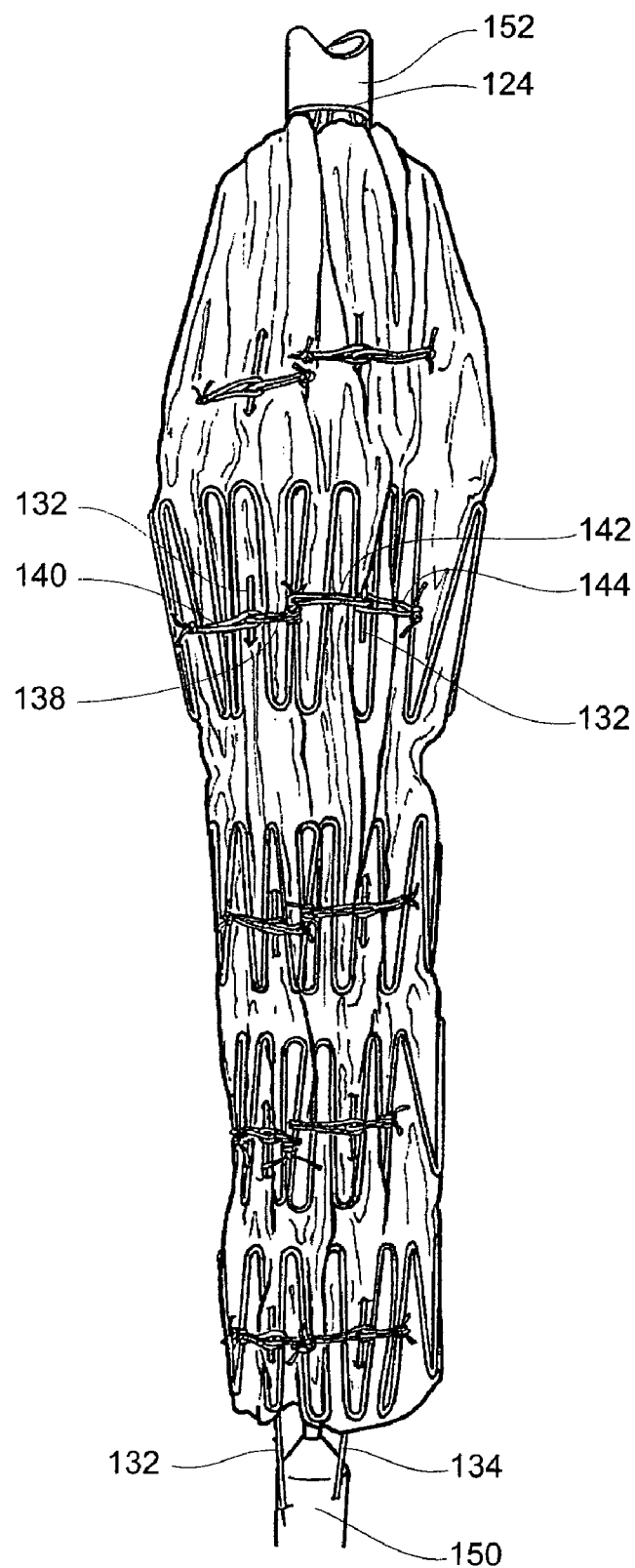
Figure 9C:
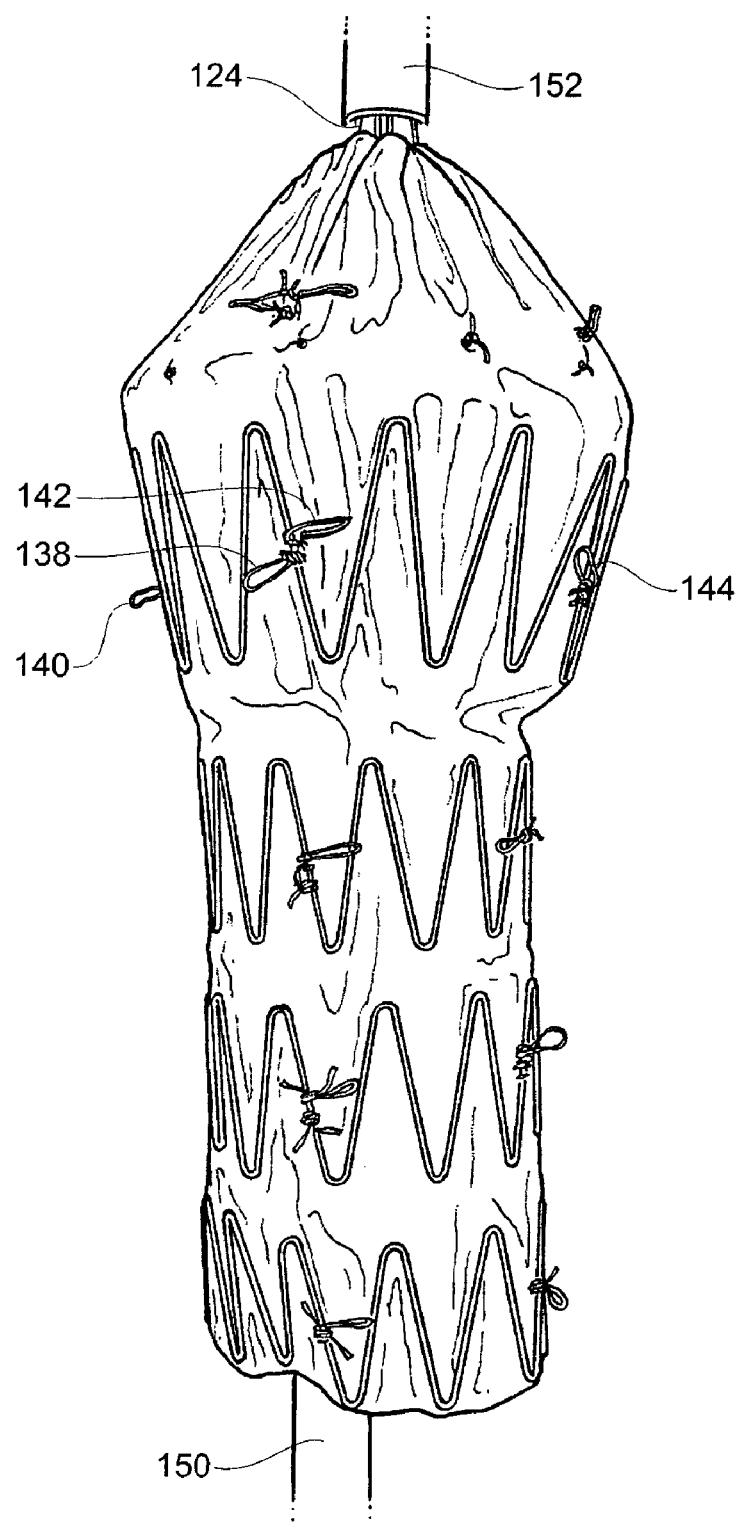

FIGS. 9A, 9B and 9C show a stent graft with various stages of fitting and release of diameter reducing ties.

As discussed earlier, diameter reducing ties are placed onto a stent graft requiring diameter reduction at a point substantially diametrically opposite to the fenestrations and hence in FIGS. 9A, 9B and 9C the fenestrations cannot be seen.

FIG. 9A shows a more proximal portion of a composite stent graft for mounting into the aorta. The stent graft includes a tubular body 120 with an internal zigzag self expanding stent 122 at its proximal end and an exposed proximally extending stent 124 mounted to the proximal end of the tubular body 120. Further external self expanding stents 126 are supplied along the length of the body to the distal end 128. It will be noted the tubular body 120 tapers at 130 so that it is a first selected diameter at the proximal end and a slightly smaller diameter further down the length of the tubular body.

This invention will be discussed particularly in relation to installation of double diameter reducing ties.

The first stage is the placement of release wires 132 and 134 which extend longitudinally along the tubular body and are stitched in and out of the tubular body. Stitches can be seen on the exterior of the tubular body in regions coinciding with the intermediate region of each of the exposed stents. In the region designated as 130 for instance a suture is placed around the release wire and extended across about three struts of the zigzag stent 126 to strut 136 and pulled tight as shown at 138 in FIG. 9B. Similarly a suture 140 extended from the other direction from the release wire 132 for about three struts and then pulled tight.

A similar extension of sutures in each direction from release wire 134 are installed to compress the other side. The suture 142 which extends back towards the release wire 132 is joined to the same strut 136 as the suture 138. The suture 144 extends in the opposite direction from the release wire 134.

This process is repeated with the other exposed stents 126 and the internal stent 122. In the case of the internal stent 122 the sutures are inserted through the material of the tubular body 120 to go around the stents where they are knotted but otherwise remain outside of the tubular body. This gives the result as shown in FIG. 9B where the diameter of the stent graft is considerably reduced. Diameter reducing ties may be either placed along the entire length of the stent graft so that the stent graft remains manoeuvrable after its partial release as discussed above or can be confined to only the parts of the stent graft that are larger in diameter than the vessel lumen into which it is to be placed.

FIG. 9B shows the stent graft mounted onto a deployment device with a pusher catheter 150 at one end and a nose cone capsule 152 into which the proximally extending stent 124 is received at the other end.

FIG. 9C shows the stent graft still mounted onto the deployment device so that the exposed stent 124 is still received in the capsule 152 but the release wires have been withdrawn so that the diameter reducing ties are released. It will be noted that the sutures 140, 138, 142, and 144 remain on the outside of the stent graft. This is not a problem as they do not interfere with blood flow and may assist with adhesion of the stent graft onto the wall of the aorta.

In an alternative arrangement where space permits two sets of double diameter reducing ties may be used with one set of double diameter reducing ties and trigger wire placed anterior to the renal arteries and another set of double diameter reducing ties and trigger wire placed posterior to the renal arteries.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A method of pre-operative sizing of a stent graft with at least two fenestrations for placement into a body vessel having an inner wall with side branch vessels and the stent graft intended for access to the side branch vessels through the fenestrations, the method comprising the steps of;
    a) determining the internal diameter of the body vessel at the level of the side branch vessels,
    b) assessing the angular position of the of each of the side branch vessels from a selected datum position on the vessel,
    c) converting the angular position to a circumferential distance along the inner wall of the vessel from the selected vessel datum to each side branch vessel for each of the branch vessels,
    d) selecting a diameter of stent graft which is 10% to 20% greater than the determined diameter of the vessel,
    e) defining a stent graft datum position on the stent graft,
    f) positioning fenestrations on the stent graft such that each is the converted distance calculated in step c) from the stent graft datum position on the stent graft;
    g) temporarily reducing the diameter of the stent graft at least at the level of the fenestrations at a position substantially diametrically opposite to the stent graft datum position and
    (h) the step of temporarily reducing the diameter comprising applying diameter reducing ties at a position diametrically opposed to the two fenestrations to give a diameter reduced portion and the diameter reduction not being applied in the region of the fenestrations;
    whereby the diameter reduced portion of the stent graft, when deployed, is as far around from the side branch vessels as possible.

2. A method as in claim 1 wherein the selected datum position on the vessel is the anterior most point in the vessel and the stent graft datum position is the anterior most position in the stent graft.

3. A method as in claim 1 wherein the internal diameter of the body vessel and the angular position of the of each of the side branches are determined with the use of narrow slice, contrast enhanced computer tomography.

4. A method as in claim 1 wherein the step of assessing the angular position of the of each of the side branches from the selected datum position on the vessel, comprises defining the angular position as a clock face with the datum position on the vessel being 12 o'clock and the position of the of each of the side branches being in terms of hours on the clock face.

5. A method as in claim 1 wherein the step of assessing the angular position of the of each of the side branches from the selected datum position on the vessel, comprises defining the angular position as degrees either side of the datum position on the vessel.

6. A method as in claim 1 wherein the step of applying diameter reducing ties comprises the steps of;
    a) stitching a release wire longitudinally along the stent graft;
    b) looping a flexible thread around the release wire and extending one end of the flexible thread laterally around the circumference of the stent graft to a position a selected distance from the release wire;

c) engaging the flexible thread into the graft material, and d) drawing the ends of the thread together and tying ends of the thread, whereby the selected distance is reduced thereby reducing the overall diameter of the stent graft.

7. A method as in claim 6 comprising the step of extending a circumferential thread in each direction from the release wire.

8. A method as in claim 6 further comprising the steps of;

e) passing a second flexible thread around the release wire or the first flexible thread and extending the second flexible thread laterally around the circumference of the stent graft in the opposite direction to the first flexible thread to a position a selected distance from the release wire;

f) engaging the second flexible thread into the graft material, and g) drawing the ends of the second thread together and tying ends of the thread, whereby the selected distance is reduced thereby reducing the overall diameter of the stent graft.

9. A method as in claim 6 wherein the stents are zig-zag stents comprising struts and bends therebetween and the engagement of the flexible thread into the graft material includes the engagement of the thread around a strut of the self expanding stent.

10. A method as in claim 1 wherein the circumferential distance is reduced by from 50 to 75%.

11. A method as in claim 1 wherein the step of applying diameter reducing ties comprises applying a plurality of diameter reducing ties to respective stents along the length of the stent graft.

12. A stent graft prepared by the method of claim 1.

* * * * *